United States Patent
Keillor

(10) Patent No.: US 10,716,549 B2
(45) Date of Patent: Jul. 21, 2020

(54) MEDICAL DEVICE FOR TREATING A TARGET SITE

(71) Applicant: AGA Medical Corporation, Plymouth, MN (US)

(72) Inventor: Matthew Keillor, Minneapolis, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 429 days.

(21) Appl. No.: 13/785,754

(22) Filed: Mar. 5, 2013

(65) Prior Publication Data

US 2014/0257360 A1 Sep. 11, 2014

(51) Int. Cl.
A61B 17/00 (2006.01)
A61B 17/12 (2006.01)

(52) U.S. Cl.
CPC .... *A61B 17/0057* (2013.01); *A61B 17/12113* (2013.01); *A61B 17/12122* (2013.01);
(Continued)

(58) Field of Classification Search
CPC .......... A61B 17/0057; A61B 17/12109; A61B 17/12172; A61B 2017/00575; A61B 2017/00606; A61B 2017/00632; A61B 17/12022; A61B 17/12113; A61B 17/12122; A61B 17/12177; A61B 17/1219; A61B 17/12118; A61B 2017/00867; A61B 2017/00592; A61B 2017/12054; A61F 2/90; A61F 2/06; A61F 2/01;
(Continued)

(56) References Cited

U.S. PATENT DOCUMENTS 5,846,261 A * 12/1998 Kotula ...................... A61F 2/01
   606/213
6,168,622 B1 * 1/2001 Mazzocchi ........ A61B 17/0057
   606/200
(Continued)

FOREIGN PATENT DOCUMENTS

WO 20130159065 10/2013

OTHER PUBLICATIONS

Definition of "Disk" accessed on Apr. 27, 2016 <http://www.dictionary.com/browse/disk>.*
(Continued)

*Primary Examiner* — Elizabeth Houston
*Assistant Examiner* — Mohamed G Gabr
(74) *Attorney, Agent, or Firm* — Armstrong Teasdale LLP

(57) ABSTRACT

Embodiments of the present disclosure are directed to medical devices for treating a target site. For example, a medical device comprises a tubular member having a proximal end and a distal end, the tubular member having an expanded preset configuration when deployed at the target site and a reduced configuration for delivery to the target site. The tubular member comprises at least one layer of braided fabric, and the at least one layer of braided fabric comprises a plurality of first strands having a first diameter and a plurality of second strands having a second diameter. The first diameter is larger than the second diameter. The plurality of first strands and the plurality of second strands are intertwined to define regions of varying radial stiffness between the proximal and distal ends of the tubular member.

25 Claims, 11 Drawing Sheets

(52) U.S. Cl.
CPC .. *A61B 17/12172* (2013.01); *A61B 17/12109* (2013.01); *A61B 2017/00526* (2013.01); *A61B 2017/00575* (2013.01); *A61B 2017/00592* (2013.01); *A61B 2017/00597* (2013.01); *A61B 2017/00606* (2013.01); *A61B 2017/00867* (2013.01)

(58) Field of Classification Search
CPC ............... A61F 2/0063; A61F 2/442; A61F 2002/0016; A61F 2002/30093; A61F 2002/0072; A61F 2002/018; A61F 2002/3008; A61F 2002/30092; A61F 2210/0019; A61F 2220/0075; A61F 2230/0006; A61F 2250/0018
USPC ......... 606/200, 151, 157, 158, 216; 623/1.1, 623/1.11, 1.23, 1.24, 1.25, 1.51
See application file for complete search history.

(56) References Cited

U.S. PATENT DOCUMENTS

| | | | |
|---|---|---|---|
| 6,346,117 B1 | 2/2002 | Greenhalgh | |
| 6,468,303 B1* | 10/2002 | Amplatz | A61B 17/11 623/1.2 |
| 8,034,061 B2* | 10/2011 | Amplatz et al. | 606/151 |
| 8,048,147 B2 | 11/2011 | Adams | |
| 2003/0135265 A1 | 7/2003 | Stinson | |
| 2003/0195553 A1 | 10/2003 | Wallace et al. | |
| 2005/0283246 A1 | 12/2005 | Cauthen III et al. | |
| 2006/0135947 A1 | 6/2006 | Soltesz et al. | |
| 2006/0241690 A1* | 10/2006 | Amplatz | A61B 17/0057 606/213 |
| 2007/0208373 A1 | 9/2007 | Zaver | |
| 2009/0018562 A1* | 1/2009 | Amplatz | A61B 17/0057 606/157 |
| 2009/0275974 A1* | 11/2009 | Marchand | A61B 17/12022 606/194 |
| 2009/0306706 A1* | 12/2009 | Osypka | A61B 17/0057 606/213 |
| 2011/0144739 A1 | 6/2011 | Cattaneo | |
| 2012/0283768 A1 | 11/2012 | Cox et al. | |
| 2012/0323267 A1 | 12/2012 | Ren | |

OTHER PUBLICATIONS

International Search Report and Written Opinion for PCT/US2013/078284 dated Apr. 17, 2014; 15 pages.

* cited by examiner

MEDICAL DEVICE FOR TREATING A TARGET SITE

BACKGROUND

I. Field of the Disclosure

The present disclosure relates generally to medical devices for treating target sites. More particularly, the present disclosure is directed to devices and methods having variable mechanical properties for treating areas within a patient's body.

II. Description of the Related Art

A wide variety of intravascular devices are used in various medical procedures. Certain intravascular devices, such as catheters and guidewires, are generally used to deliver fluids or other medical devices to specific locations within a patient's body, such as a select site within the cardiovascular system. Other, frequently more complex devices are used to treat specific conditions, such as devices used to occlude a target site.

BRIEF SUMMARY

Embodiments of the present disclosure are directed to medical devices, systems, and methods for treating a target site. In one embodiment, a medical device for treating a target site includes a tubular member having a proximal end and a distal end, wherein the tubular member has an expanded configuration when deployed at the target site and a reduced configuration for delivery to the target site. The tubular member comprises at least one layer of braided fabric, and the at least one layer of braided fabric includes a plurality of first strands having a first diameter and a plurality of second strands having a second diameter. The first diameter is larger than the second diameter. The plurality of first strands and the plurality of second strands are intertwined with one another to define the at least one layer of braided fabric, wherein the plurality of first strands intersect one another at one or more locations between the proximal and distal ends of the tubular member to define at least one region of increased stiffness in relation to one or more locations where the plurality of first strands do not intersect one another.

According to another embodiment, a medical device for treating a target site comprises a plurality of first strands having a first diameter and a plurality of second strands having a second diameter smaller than the first diameter. The plurality of second strands are intertwined with the plurality of first strands to define at least one layer of braided fabric having regions of varying radial stiffness. The medical device further includes a tubular member formed from the at least one layer of braided fabric, wherein the tubular member has an expanded configuration for deployment at the target site and a reduced configuration for delivery to the target site.

In another embodiment, a medical device for treating a target site comprises a plurality of first strands having a first diameter and a plurality of second strands having a second diameter smaller than the first diameter. The plurality of second strands are intertwined with the plurality of first strands to define at least one layer of braided fabric having a braid pattern. The medical device also includes a tubular member formed from the at least one layer of braided fabric, wherein the tubular member has an expanded configuration for deployment at the target site and a reduced configuration for delivery to the target site. The tubular member comprises at least one disk in the expanded configuration, wherein the disk comprises at least one stiff region and at least one soft region resulting from the braid pattern of the first and second strands.

According to one embodiment, a method of manufacturing a medical device is provided. The method comprises braiding a plurality of first strands and a plurality of second strands to define a tubular member having at least one layer of braided fabric. The plurality of first strands have a first diameter and the plurality of second strands have a second diameter, wherein the first diameter is larger than the second diameter. The method further includes heat setting the tubular member to define an expanded preset configuration, wherein the tubular member has a proximal end and a distal end. The braiding step comprises braiding the plurality of first strands such that the plurality of first strands intersect one another at one or more locations between the proximal and distal ends of the tubular member to define regions of varying radial stiffness between the proximal and distal ends of the tubular member.

BRIEF DESCRIPTION OF THE DRAWINGS

The foregoing features and advantages of embodiments in accordance with the present disclosure will become apparent to those skilled in the art from the following detailed description, especially when considered in conjunction with the accompanying drawings in which like numerals in the several views refer to corresponding parts.

DETAILED DESCRIPTION

Figure 1:
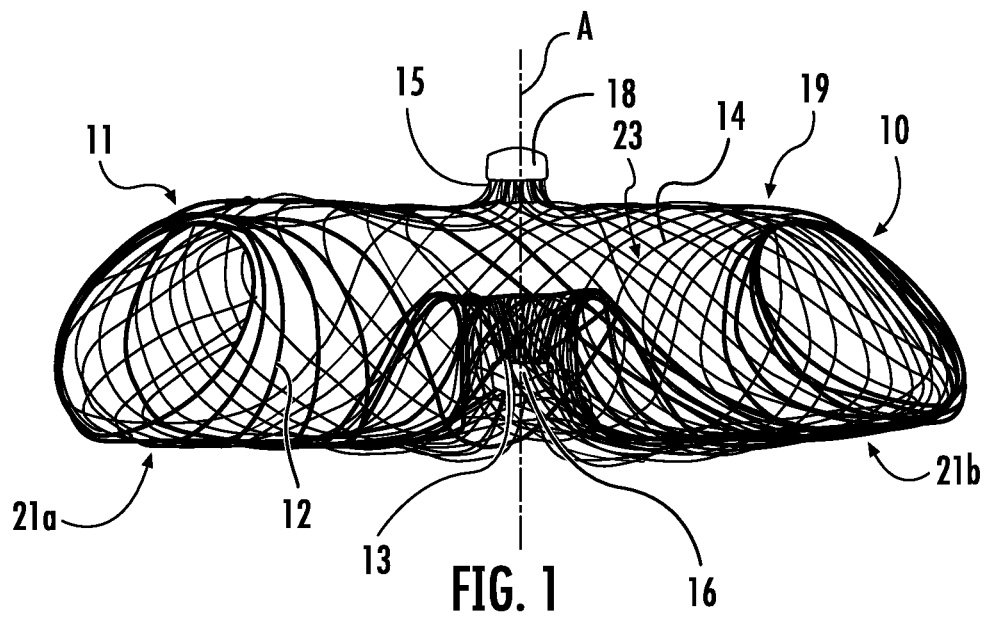
FIG. 1 is an side view of a medical device according to an embodiment of the present disclosure.

Several factors affect the effectiveness of a medical device to treat a target site, such as the particular geometry and flexibility of the medical device. For example, a medical device suitable for treating one target site may be unsuitable for treating another target site. Thus, the geometry of the medical device may be modified to treat particular target sites. In addition, the medical device may undergo particular manufacturing process, such as heat treatment, to create different mechanical properties. However, additional customization beyond modification to the geometry or manufacturing process of the medical device may be necessary to more effectively treat a target site.

Therefore, it would be advantageous to provide a medical device that facilitates further customization of the properties of the medical device for more effectively treating a target site.

As described in greater detail below, medical devices in accordance with the present disclosure are configured to treat a target site. In one embodiment, a medical device is configured to include regions of variable stiffness. Thus, the medical device may provide greater flexibility in customizing the mechanical properties of the medical device for treating particular target sites. For example, the medical device may be suitable for target sites requiring both stiff and soft regions to provide adequate support and retention due to the stiff regions, while providing greater flexibility with the soft regions where little or no contact with the target site is needed.

It is understood that the use of the term "target site" is not meant to be limiting, as the medical device may be configured to treat any target site, such as an abnormality, a vessel, an organ, an opening, a chamber, a channel, a hole, a cavity, a body lumen, a valve, or the like, located anywhere in the body. The medical device may be suitable for selective occlusion of a target site anywhere in the body's circulatory system where it is desired to stop the flow of blood. The medical device may also be deployed in a variety of manners with respect to a target site, such a proximate or adjacent to the target site, at the target site, or within the target site. Moreover, although examples are provided of a medical device that is used for treating a target site within the circulatory system, such as for the closure of an aortic valve or atrial or ventricle septal defects, it is understood that embodiments of the medical device may be used for various applications. In addition, although the medical device is herein described in connection with a delivery device, it is further understood that the medical device may be used with other catheters, delivery sheathes, device loaders, and other accessories. As also used herein, the term "proximal" refers to a portion of the referenced component of a medical device that is closest to the operator, and the term "distal" refers to a portion that is farthest away from the operator at any given time as the medical device is delivered to the target site.

Embodiments of the present disclosure are described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Figure 1A:
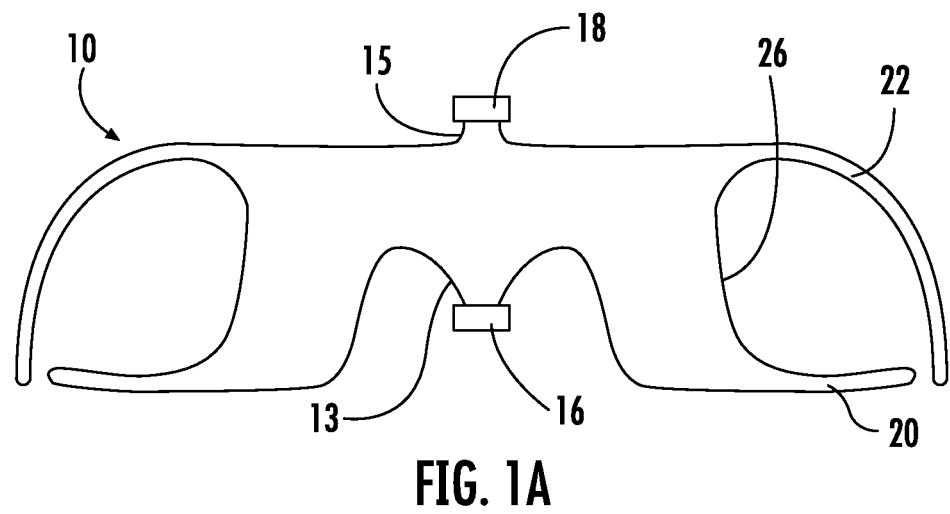
FIG. 1A is a cross-sectional view of the medical device from FIG. 1.
Figure 2:
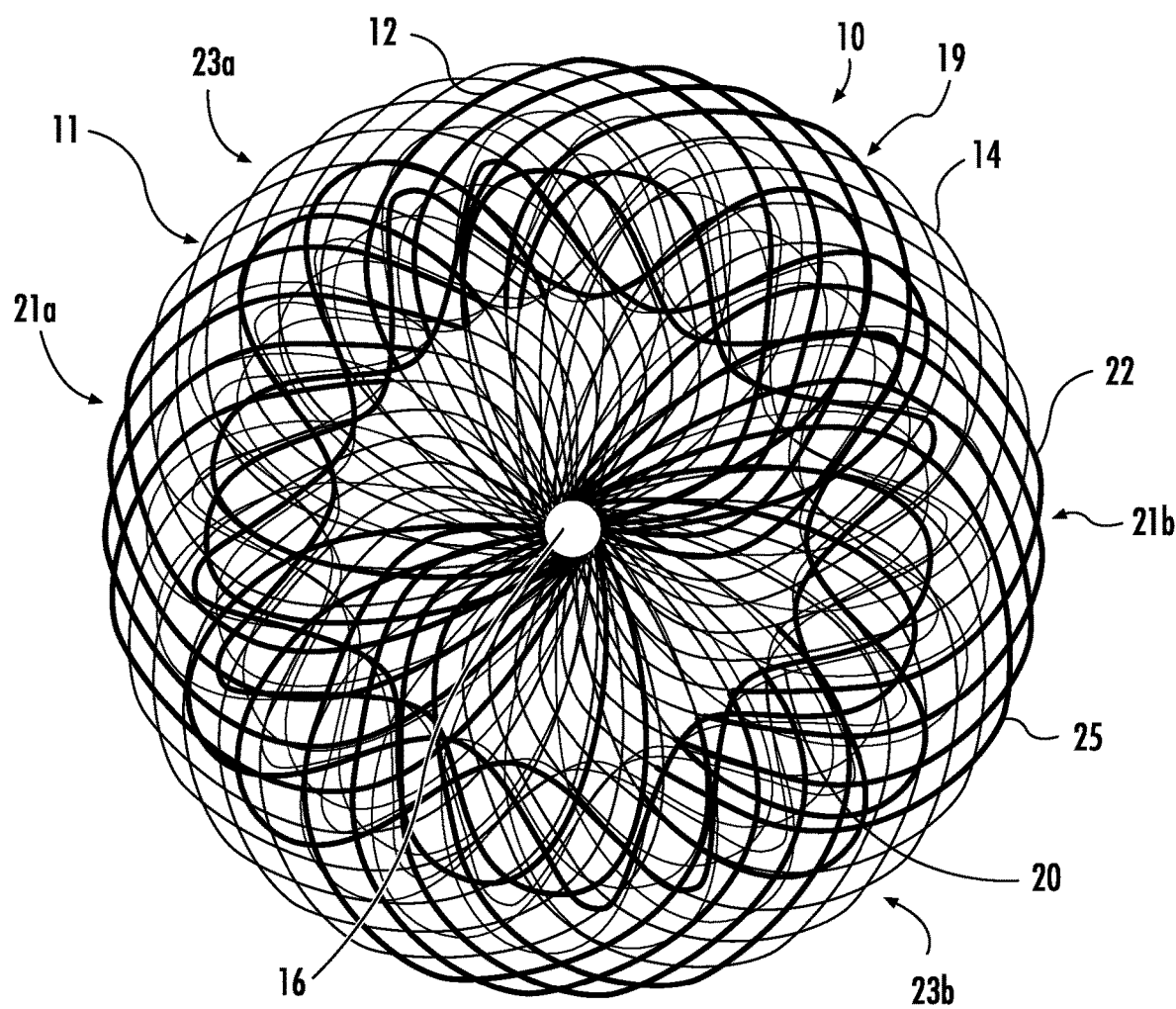
FIG. 2 is an end view of the medical device from FIG. 1.

Turning now to the specific embodiments set forth in the accompanying drawings. FIGS. 1, 1A, and 2 depict one embodiment of medical device 10, which is configured to treat a target site, such as a target site in a patient's body. Embodiments of medical device 10 generally comprise tubular member 11 having a plurality of first strands 12, proximal end 13, a plurality of second strands 14, and distal end 15. Proximal end 13 of tubular member 11 is secured by proximal clamp 16 (terminal member 16), while distal end 15 of tubular member 11 is secured by distal clamp 18 (terminal member 18). Proximal clamp 16 may be configured to engage a delivery device, as further detailed below with reference to FIG. 15.

Tubular member 11 comprises at least one disk, wherein FIG. 1A shows two disks, proximal disk 20 and distal disk 22 separated by waist 26, with proximal disk 20 nested within distal disk 22. FIGS. 1 and 2 illustrate disks 20, 22 in a relaxed state or expanded configuration. In addition, FIG. 1 illustrates that distal disk 22 may have a generally frustoconical shape in the expanded, configuration. In addition, FIG. 1A shows that proximal disk 20 may have a generally disk shape, wherein proximal disk 20 has a smaller outer diameter than distal disk 22. Proximal disk 20 is surrounded by distal disk 22 and separated by a central waist 26. The outer diameter of waist 26 is smaller than outer diameter of disks 20, 22. Waist 26 may be configured for placement within an opening at a target site and/or facilitating alignment between disks 20, 22 at the target site. Thus, the length and outer diameter of waist 26 may approximate the length and/or inner diameter of the opening of the target site, while disks 20, 22 may be configured to overlie opposing sides of the opening. FIG. 1A also illustrates that distal disk 22 may be recessed or otherwise define a concave shape such that waist 26 and proximal disk 20 are at least partially surrounded by distal disk 22. FIG. 1A further illustrates that waist 26 may be recessed such that proximal clamp 16 is at least partially surrounded by waist 26. Thus, a smaller axial dimension between proximal 13 and distal 15 ends may be achieved.

As used herein, the term "disk" is not meant to be limiting and may be a member or lobe having a circular, an oval, a conical, a frustoconical, a discoid, or other shape having a cross-sectional dimension configured to overlie or engage a target site, such as for substantially precluding or impeding flow through an opening at the target site. Although FIG. 1 illustrates tubular member 11 with two disks 20, 22, it is understood that tubular member 11 may have one or more disks 20, 22 depending on the target site and particular application.

Tubular member 11 may have a preset configuration in a relaxed state, such as an expanded configuration for deployment at a target site, and be configured to be constrained to a reduced configuration for delivery to the target site whereupon tubular member will at least partially return to its preset configuration. For example, tubular member 11 may be heat set in a particular configuration and if formed of a shape-memory material, may be biased such that tubular member 11 is configured to self expand from the reduced configuration and return towards the preset configuration.

Figure 3:
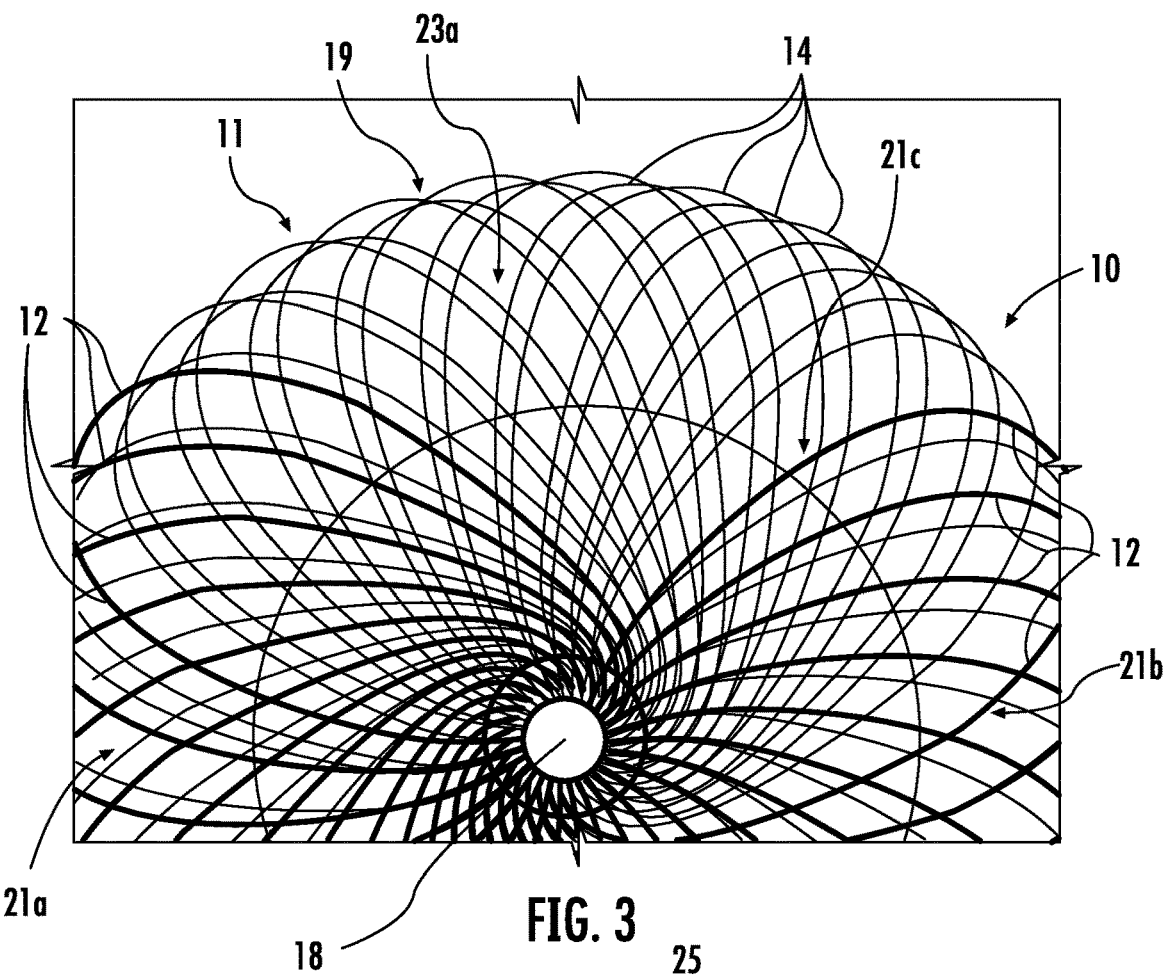
FIG. 3 is an enlarged end view of the medical device from FIG. 1.

Tubular member 11 may be formed of braided fabric 19 comprising a plurality of first strands 12 and second strands 14 (see e.g., FIGS. 1-3). Although the term "tubular" is used, it is understood that tubular member 11 may be braided into a continuous tubular body, a tubular body with one open and one closed end, comprise a sheet of material that is formed into a tubular shape, or be otherwise formed. In addition, tubular member 11 may comprise one or more layers of braided fabric 19. According to one embodiment of the present disclosure, tubular member 11 includes braided fabric 19 formed of a plurality of first strands 12 and second strands 14, wherein each of strands 12, 14 has a predetermined relative orientation with respect to one another (e.g., a helical braid). Moreover, medical device 10 may comprise a plurality of layers of braided fabric 19 and/or other occluding material such that the device is capable of at least partially inhibiting blood flow therethrough in order to facilitate the formation of thrombus and epithelialization around medical device 10. Although the term "strand" is discussed herein, "strand" is not meant to be limiting, as it is understood tubular member 11 may comprise one or more wires, cords, fibers, yarns, filaments, cables, threads, or the like, such that these terms may be used interchangeably. Strands 12, 14 may be braided, interwoven, or otherwise combined to define generally tubular member 11. One may solder, braze, weld, coat, glue, clamp, tie or otherwise affix the ends of braided strands 12, 14 together, such as with marker bands or clamps 16, 18 shown in FIGS. 1 and 2. Thus, the term "clamp" is also not meant to be limiting, as any suitable securement method or mechanism may be used to prevent the ends of strands 12, 14 from unraveling.

One of clamps 16, 18 may include an engagement member (not shown) for facilitating attachment with a delivery device. For example, proximal clamp 16 at proximal end 13 of tubular member 11 may have a threaded internal bore that is sized and configured for receiving an externally threaded delivery device. Thus, proximal clamp 16 may be configured as an internally threaded end screw for receiving and engaging a delivery device in a threaded engagement such that rotation of the delivery device in a clockwise or counterclockwise direction facilitates attachment to and detachment from proximal clamp 16 depending on the direction in which the delivery device is rotated. It is understood that the engagement between proximal clamp 16 and delivery device is not meant to be limiting, as the threads may be reversed such that proximal clamp 16 is externally threaded and delivery device is internally threaded. In some cases, distal clamp 18 may also or alternatively be configured for releasable attachment to a delivery device. Furthermore, other suitable techniques may be used to engage and disengage clamps 16, 18 from delivery device in response to manipulation of delivery device while providing the ability to transmit torque, such as a press fit, snap fit, twist-fit, and the like.

Strands 12, 14 of a metal fabric used in one embodiment may be formed of a material that is both resilient and that can be heat treated to substantially set a desired preset shape. One class of materials which meets these qualifications is shape memory alloys. One example of a shape memory alloy is Nitinol. It is also understood that strands 12, 14 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, strand 12, 14 diameter, number of strands 12, 14, and pitch may be altered to achieve the desired properties of medical device 10.

In one embodiment, first strands 12 have a larger diameter than second strands 14. In this regard, FIGS. 1 and 2 illustrate that strands 12, 14 are intertwined, braided, or woven to intersect one another at one or more locations between proximal 13 and distal 15 ends of tubular member 11. For example, in locations where first strands 12 intersect, stiff regions 21a, 21b are formed. Further, there are soft regions 23a and 23b where second strands 14 intersect and/or where first strands 12 are absent. Thus, medical device 10 is configured to include regions of variable stiffness. Therefore, medical device 10 may be suitable for target sites requiring both stiff regions 21a, 21b and soft regions 23a and 23b to provide adequate support and retention due to the stiff regions 21a, 21b, while providing greater flexibility with the soft regions 23 where little or no contact with the target site is needed.

FIG. 3 is an enlarged view of medical device 10 from FIGS. 1-2 and also illustrates that strands 12, 14 are intertwined, braided, or woven to intersect one another at one or more locations to define at least one stiff region 21a, 21b and at least one soft region 23 between proximal 13 and distal 15 ends of tubular member 11. In particular, strands 12, 14 define at least one stiff region 21a, 21b of increased radial stiffness where first strands 12 intersect one another. Regions where first strands 12 are located but do not intersect one another may also define one or more stiff regions 21c. For example, stiff regions 21c may be defined in locations where first strands 12 intersect second strands 14 as shown in FIG. 3. Likewise, soft regions 23a may be defined where second strands 14 intersect one another or where first strands 12 are not located. Thus, strands 12, 14 are intertwined to define regions of varying radial stiffness between proximal 13 and distal 15 ends of tubular member 11. FIG. 3 shows that first strands 12 may intersect, cluster, or otherwise associate at a plurality of locations to define a plurality of corresponding stiff regions. FIGS. 1-3 further illustrate that first strands 12 may intersect one another at radially opposite locations, first stiff region 21a and second stiff region 21b, with respect to central axis "A" of tubular member 11 that extends between proximal 13 and distal 15 ends (shown in FIG. 1). In another embodiment, first strands 12 may additionally or alternatively intersect one another at a plurality of co-linear locations between proximal 13 and distal 15 ends of tubular member 11 (see e.g., FIGS. 9-11). Moreover, first strands 12 may intersect one another at least partially along outer perimeter 25 of tubular member 11, as shown in FIG. 2. Thus, first strands 12 may intersect at least partially along outer perimeter 25 of one or both of disks 20, 22.

Second strands 14 have a smaller diameter than first strands 12. Soft regions 23 are formed by the lack of stiff regions 21a, 21b, 21c and/or clustering of first strands 12, as well as the lack of intersection of first strands 12 and/or the intersection of second strands 14. For example, FIG. 2 further illustrates that second strands 14 may intersect one another at radially opposite locations to define first soft region 23a and second soft region 23b, with respect to central axis "A" of tubular member 11. In one embodiment, second strands 14 may intersect one another at a plurality of co-linear locations between proximal 13 and distal 15 ends of tubular member 11 in locations where first strands 12 are not located (see e.g., FIGS. 9-11). Moreover, similar to first strands 12, second strands 14 may intersect one another at least partially along outer perimeter 25 of tubular member 11, as shown in FIG. 3. Thus, second strands 14 may intersect at least partially along outer perimeter 25 of one or both of disk 20, 22.

As discussed above, first strands 12 have a larger diameter than second strands 14. According to some embodiments, a ratio of the diameter of first strands 12 to second strands 14 is at least about 1.5:1, at least about 2:1, at least about 3:1, at least about 4:1, or at least about 5:1. For example, diameter of first strands 12 may be about 0.0055 inches (0.1397 mm) or 0.006 inches (0.152 mm), while diameter of second strands 14 may be about 0.003 inches (0.076 mm). In addition, although first strands 12 and second strands 14 are described as having different diameters, it is understood that there may a plurality of strands of varying diameter (e.g., 2, 3, 4, 5, or 6 different strand diameters).

Figure 4:
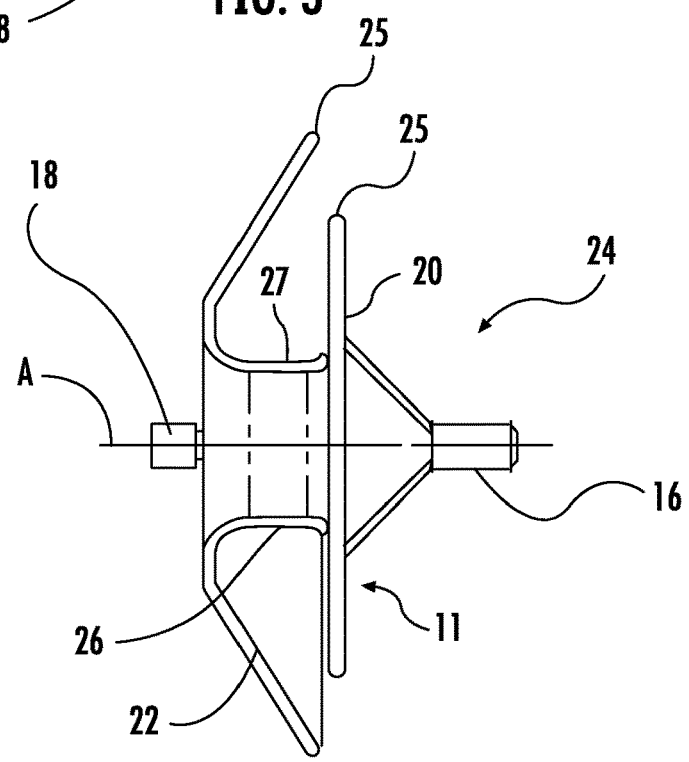
FIG. 4 is a cross-sectional view of a medical device according to another embodiment of the present disclosure.

FIG. 4 illustrates another embodiment of medical device 24. Similar to medical device 10, medical device 24 includes tubular member 11, proximal clamp 16, distal clamp 18, distal disk 22, and proximal disk 20. FIG. 4 shows that distal disk 22 has a frustoconical shape and proximal disk 20 has a disk shape, wherein distal disk 22 is angled toward disk proximal 22, although as discussed above, disks 22, 24 may be any desired shape. Disks 20, 22 may have different diameters as shown in FIG. 4. For example, the outer diameter of distal disk 22 maybe larger than that of proximal disk 20. Smaller proximal disk 20 is sized and configured to be partially surrounded by and conform to larger distal disk 22 in the relaxed state such that proximal disk 20 is nested within distal disk 22 (e.g. see FIG. 1). Thus, when positioned on opposite sides of an opening at a target site, disks 20, 22 may be configured to overlie and be biased towards one another to compress against opposite sides of the opening. Alternatively, disks 20, 22 may be sized and configured for placement within a target site such that the outer perimeter of distal disk 22 engages the target site.

FIG. 4 further illustrates that disks 20, 22 are coupled by reduced diameter waist 26, wherein the outer diameter of waist 26 is smaller than outer diameter of disks 20, 22. Waist 26 may be configured for placement within an opening at a target site and/or facilitating alignment between disks 20, 22 at the target site. Thus, the length and outer diameter of waist 26 may approximate the length and/or inner diameter of the opening of the target site, while disks 20, 22 may be configured to overlie opposing sides of the opening. FIG. 4 also illustrates that distal disk 22 may be recessed or otherwise define a concave shape such that waist 26 is at least partially surrounded by distal disk 22, which may facilitate compression between disks 20, 22 when positioned within an opening. In this regard, disks 20, 22 are able to be placed closer together than would be possible if waist 26 was not surrounded by disk 20. Thus, a compressive force between disks 20, 22 is obtainable when waist 26 is positioned within an opening, and the distance between the disks 20, 22 may be less than a thickness of the target site such that the disks are biased towards one another to be clamped to the target site. Medical device 24 may include one or more stiff regions 21*a*, 21*b*, 21*c* and soft regions 23, 23*a* as discussed above (not shown in FIG. 4). For example, stiff regions 21*a*, 21*b*, 21*c* may be provided along outer perimeter 25 of one or both disks 20, 22 and/or along outer perimeter 27 of waist 26. With respect to disks 20, 22, stiff regions 21*a*, 21*b*, 21*c* may be provided at outer perimeter 25 where disks 20, 22 have a maximum diameter. Thus, medical device 24 may be customizable to include regions of variable stiffness. In regions where additional retention is required, such as along outer perimeter 25 of disks 20, 22, stiff regions 21*a*, 21*b*, 21*c* may be provided.

Figure 5:
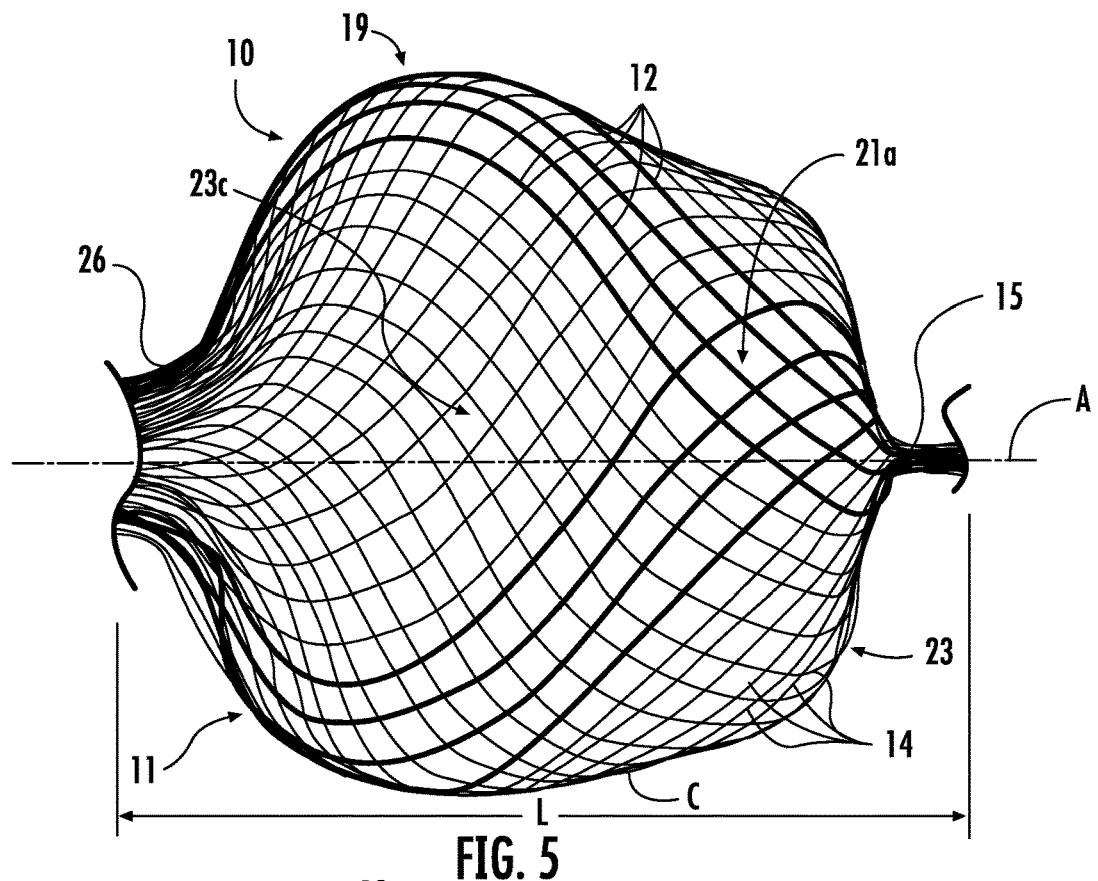
FIG. 5 is an enlarged schematic illustration of a portion of a medical device according to one embodiment of the present disclosure.
Figure 6:
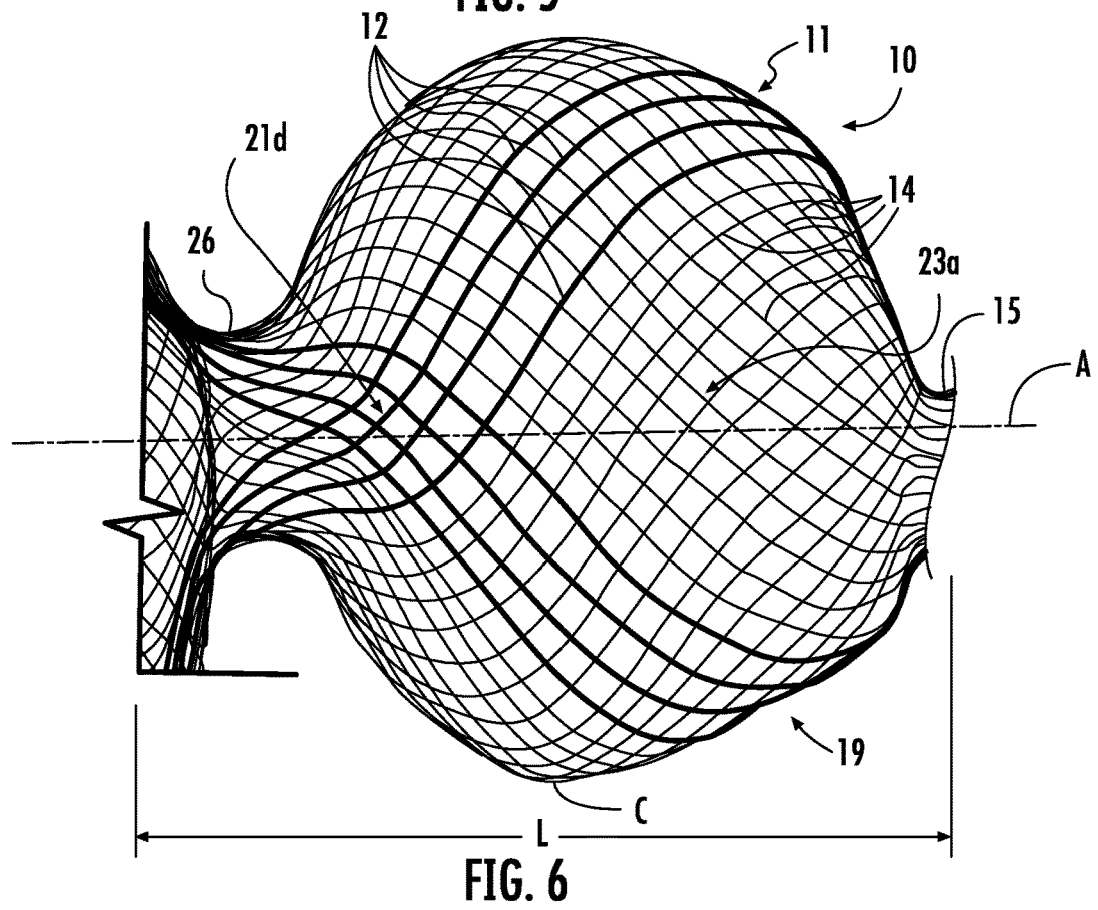
FIG. 6 is another enlarged schematic illustration of another portion of the medical device from FIG. 5.

FIGS. 5 and 6 illustrate portions of medical device 10 from FIGS. 1-3 in a partially reduced configuration according to some embodiments. In this regard, FIGS. 5 and 6 show tubular member 11 formed of braided fabric 19 including first strands 12 and second strands 14, wherein first strands 12 have a larger diameter than second strands 14 as discussed above with reference to FIGS. 1-3. FIGS. 5 and 6 show that first 12 and second 14 strands extend helically and generally parallel to one another about central axis A of tubular member 11. Because first strands 12 do not intersect one another about entire circumference "C" of tubular member 11 or along entire length "L" of tubular member 11, tubular member 11 exhibits asymmetrical radial stiffness. More specifically, regions where only second strands 14 of smaller diameter intersect and/or where first strands 12 of larger diameter do not intersect will be softer than regions where first strands 12 of larger diameter intersect. FIGS. 5 and 6 illustrate in more detail examples of locations of stiff regions and soft regions. In this regard, FIG. 5 shows stiff region 21*a* near distal end 15 of tubular member 11, while FIG. 6 shows stiff region 21*d* proximate to waist 26 of tubular member 11. Soft region 23*c* is defined between stiff region 21*a* and waist 26 in FIG. 5, while soft region 23*a* is defined near distal end 15 in FIG. 6. Thus, stiff regions 21*a*, 21*b*, 21*c*, 21*d* and soft regions 23*a*, 23*b*, 23*c* may be at any desired location on tubular member 11 depending on the braiding technique employed, as explained in further detail below (see FIGS. 12-14). As such, medical device 10 may be suitable for target sites requiring both stiff regions 21*a*, 21*b*, 21*c*, 21*d* and soft regions 23, 23*a*, 23*b*, 23*c* to provide adequate support and retention due to the stiff regions 21*a*, 21*b*, 21*c*, 21*d*, while providing greater flexibility with the soft regions 23, 23*a*, 23*b*, 23*c* where little or no contact with the target site is needed or desired.

Figure 7:
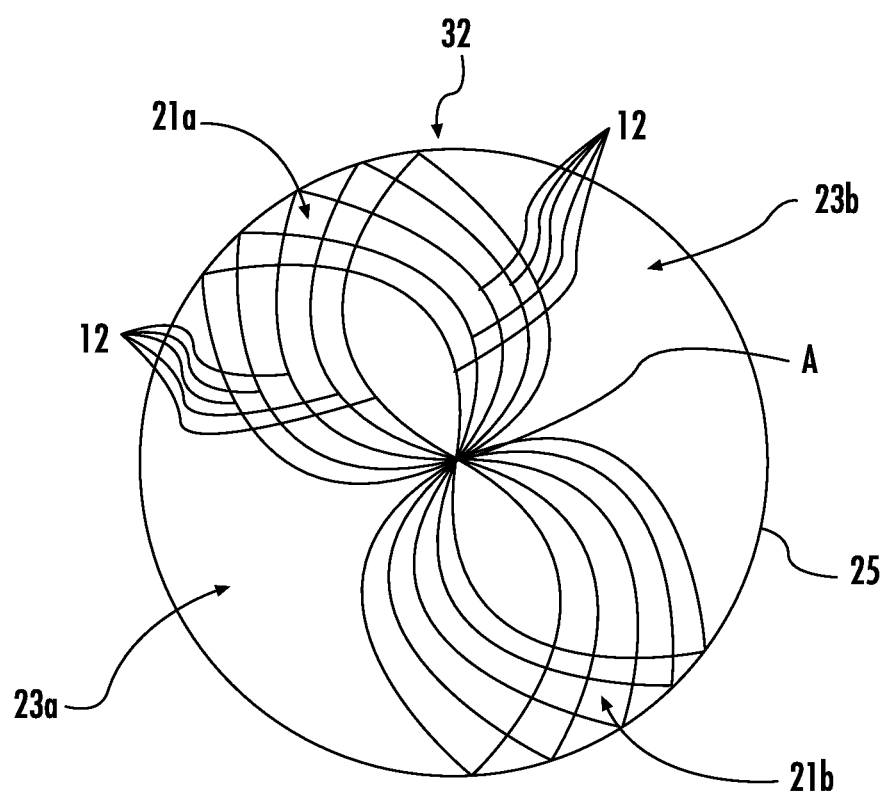
FIG. 7 is a partial end view of a medical device according to one embodiment of the present disclosure.

FIG. 7 shows an example end view of medical device 32 having first strands 12 and second strands 14 although second strands 14 are not shown for clarity of illustration. In this example, first strands 12 extend outwardly from central axis "A" and cross over one another at radially opposite locations to define stiff regions 21*a*, 21*b*. The regions where first strands 12 do not intersect, or are otherwise not located, define soft regions 23*a*, 23*b*. As such, stiff regions 21*a*, 21*b* and the soft regions 23*a*, 23*b* are disposed radially opposite from one another (e.g., stiff regions 21*a*, 21*b* and soft regions 23*a*, 23*b* are offset 90 degrees with respect to one another). As shown and as described above with respect to FIGS. 2-3, stiff regions 21*a*, 21*b* may be provided along outer perimeter 25 of medical device 32. The particular braid pattern used to define the locations of the first 12 and second 14 strands may be customizable depending on the particular braiding technique used (see FIGS. 12-14 below). Thus, the arc shaped pattern of first strands 12 shown in FIG. 7 may be any desired curvature depending on the particular braiding technique used.

Figure 8:
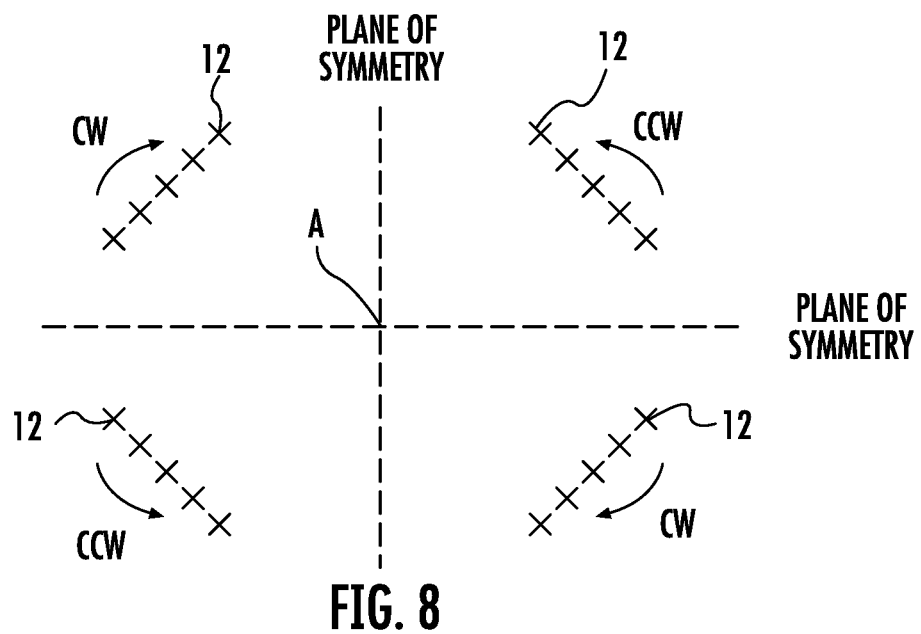
FIG. 8 is a schematic illustration of a braiding technique according to one embodiment of the present disclosure.
Figure 9:
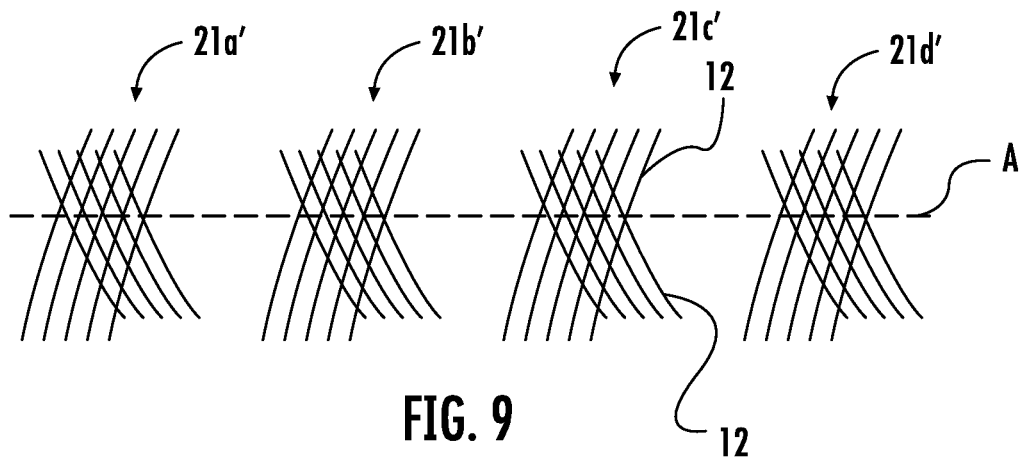
FIG. 9 is a schematic illustration of a braid pattern of a medical device having a plurality of stiff regions according to one embodiment of the present disclosure.

Various techniques may be used to manufacture medical devices discussed in accordance with the above embodiments. For example, FIG. 8 illustrates four groups of first strands 12, with two groups being wound clockwise, and two groups being wound counterclockwise. Each group of first strands 12 is separated by a plane of symmetry defined with respect to central axis A and is wound with respect to the planes of symmetry to form a braided tubular member as discussed in greater detail below. Thus, groups of first strands 12 may be wound helically in clockwise and counterclockwise directions with respect to the planes of symmetry about central axis A to define a braided fabric 19 (see FIGS. 1-3, 5, and 6). In this particular embodiment, each group includes five first strands 12, although one or more first strands 12 per group may be used if desired. When the groups of first strands 12 are wound helically in both clockwise and counterclockwise directions, first strands 12 will intersect one another at one or more locations along central axis A as shown in FIG. 9 (second strands 14 are not shown for clarity of illustration). The intersections of strands 12 define stiff regions 21*a*', 21*b*', 21*c*', 21*d*' as discussed above. Thus, the intersection of first strands 12 may occur at one or more locations along central axis A to thereby define stiff regions 21a', 21b', 21c', 21d'. Although four groups of first strands 12 and five strands within each group are discussed above in conjunction with FIGS. 8 and 9, it is understood that any number of groups and strands may be used depending on the desired mechanical properties. For example, in one embodiment, one strand 12 and one group may be employed.

Figure 10:
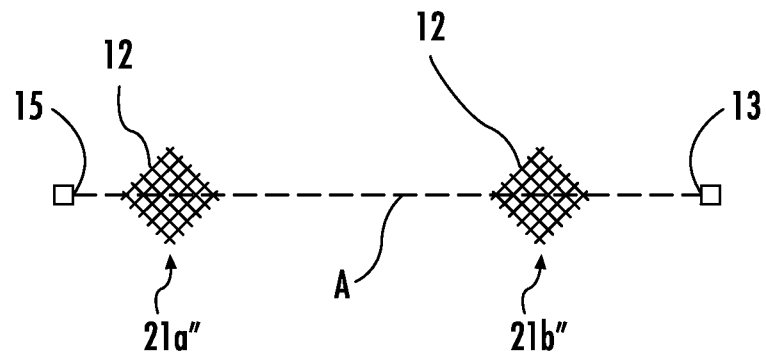
FIG. 10 is a partial schematic illustration of a medical device including a plurality of stiff regions according to an embodiment of the present disclosure.
Figure 11:
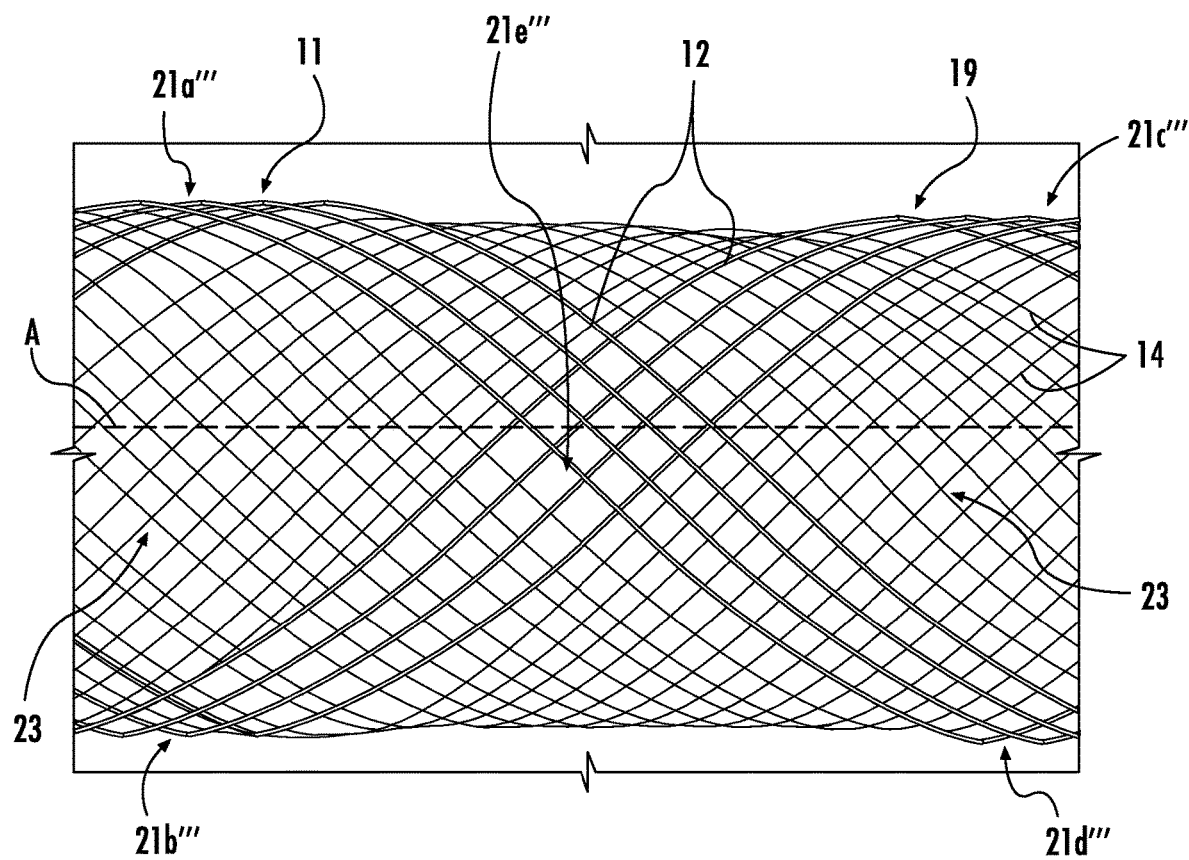
FIG. 11 is an enlarged side view of a medical device according to one embodiment of the present disclosure.

FIGS. 10 and 11 illustrate tubular member 11 formed of first strands 12 and second strands 14. First 12 and second 14 stands may be intertwined to form braided fabric 19, as discussed above with reference to FIGS. 1-3. First strands 12 may intersect at locations that are co-linear to one another along axis A defined between proximal 13 and distal ends 15 of tubular member 11. FIG. 10 shows that at least a pair of stiff regions 21a", 21b" may be formed, and the co-linear locations for stiff regions 21a", 21b" may be equidistantly spaced apart from one another or may have any desired spacing with respect to one another and proximal 13 and distal 15 ends depending on the desired shape and properties of the medical device. For example, the intersections of first strands 12 may occur along outer perimeter 25 of disks 20, 22 and/or along outer perimeter 27 of waist 26 as discussed above in connection with FIGS. 3-4. Likewise, FIG. 11 illustrates that stiff regions, 21a''', 21b''' may be formed radially opposite one another with respect to axis A, and stiff regions 21c''', 21d''' may also be formed radially opposite one another and at an offset axial location along axis A. In addition, stiff region 21e''' may be formed along axis A between stiff regions 21a''', 21b''', 21c''', 21d'''. In addition, first strands 12 may intersect at radially opposite locations as shown in FIGS. 2, 3, and 7. Therefore, the medical device may exhibit asymmetric radial stiffness with respect to central axis A (see FIG. 11) but symmetric axial stiffness along central axis A (see FIG. 10), which allows the mechanical properties of the medical device to be varied for a particular target site.

Figure 12:
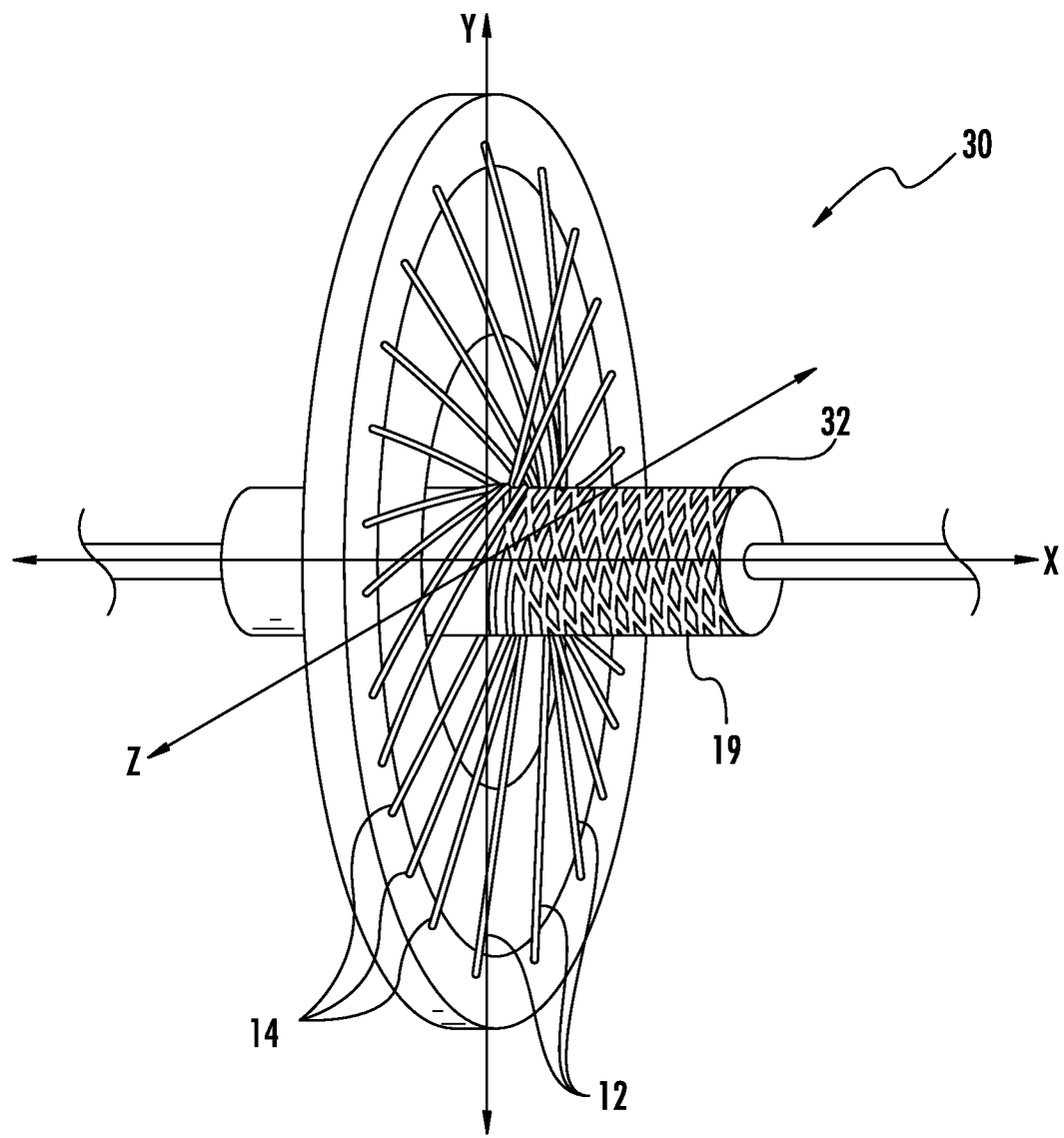
FIG. 12 is a schematic illustration of a portion of a braiding machine for braiding strands onto a mandrel according to one embodiment of the present disclosure.

In general, embodiments of tubular member 11 may be formed from braided fabric 19, which is formed using braiding machine 30 which intertwines sets of strands 12, 14 onto mandrel 32, as illustrated in FIG. 12. Mandrel 32 is disposed along longitudinal axis "X", while strands 12, 14 are braided circumferentially about mandrel 32 with respect to longitudinal axis X. Strands 12, 14 are disposed circumferentially with respect to one another such that helically winding strands 12, 14 about mandrel 32 along longitudinal axis X forms braided fabric 19, which is used to create tubular member 11 described above. As strands 12, 14 travel in a circular direction about mandrel 32, strands 12, 14 also change radius of travel to thereby wrap about mandrel 32 such that strands 12, 14 are woven over and under each other in a braided configuration. As the strands 12, 14 are wound, mandrel 32 may be moved along longitudinal axis X to set the pitch of the braided wires. For example, the pitch angle may range from about 30-70 degrees with respect to longitudinal axis X. The pitch, pick count (i.e., the number of strand crossovers per inch, or other lineal measure), and wire diameter are some variables that can be altered to change the device characteristics.

Figure 13:
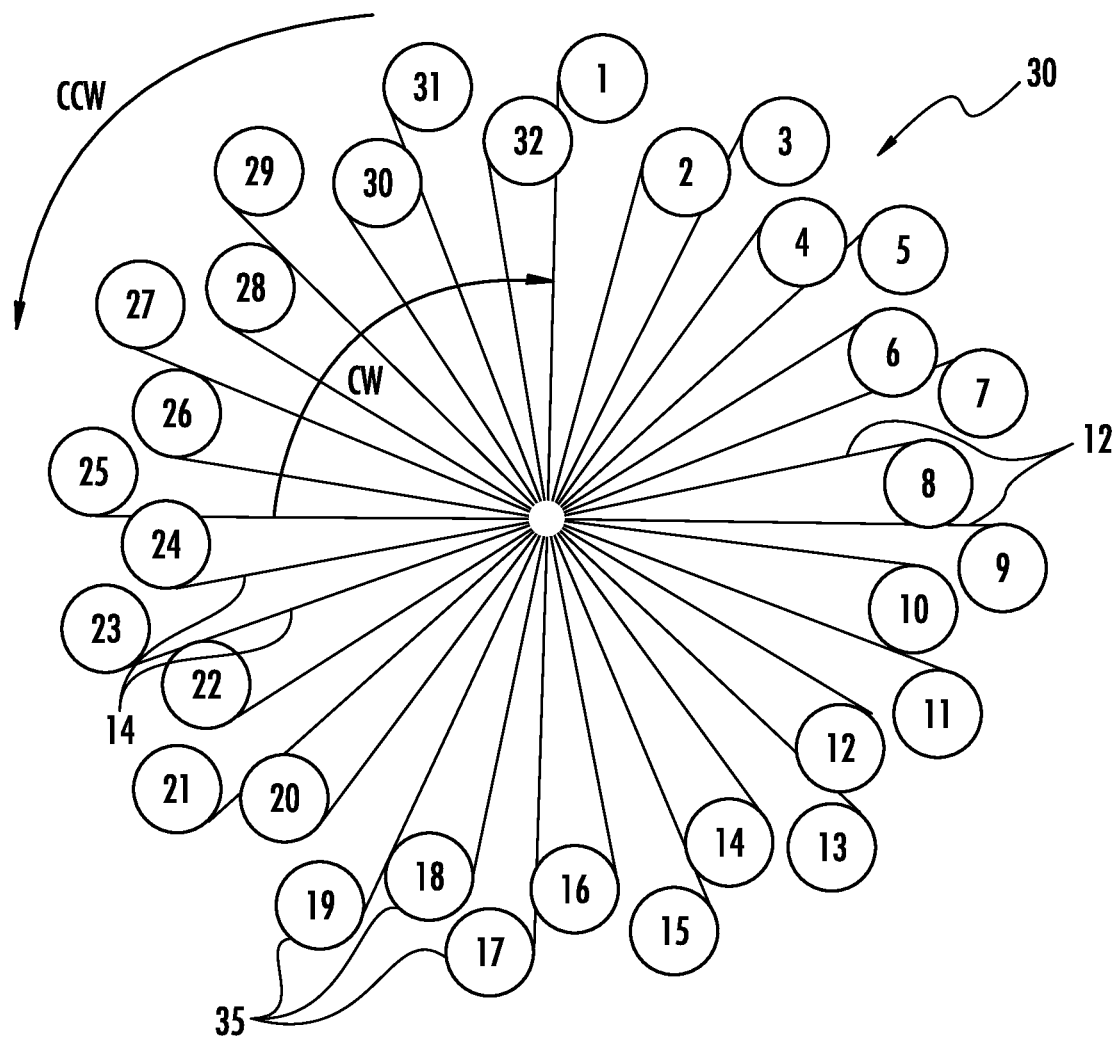
FIG. 13 is a schematic illustration of a braiding machine including a number of carriers for braiding strands onto a mandrel according to one embodiment of the present disclosure.

With reference to FIG. 13, for example, rotating spool carriers 35 may be provided, where each spool carrier 35 is configured to carry at least one spool of strands 12 or 14. In some cases, however, one or more spool carriers 35 may be left intentionally empty, or a carrier 35 may hold one or more spools according to the particular braid pattern desired. For example, the number and location of strands 12, 14 may be varied to achieve a desired stiffness and shape (e.g., such as medical device 10 shown in FIGS. 1-3). In FIGS. 12 and 13, braiding machine 30 is shown as holding 32 spool carriers 35 (numbered 1-32); however, any number of spool carriers 35 (e.g., 32, 72, etc.) and strands 12, 14 (e.g., 4-200) may be used according to the specific configuration of braiding machine 30, the desired characteristics of the resulting tubular member 11, and/or the user's preferences.

For example, in an instance where 72 carriers are employed, 20 carriers may include first strands 12, while the remaining carriers 35 (i.e., 52 carriers) may include second strands 14. In another example where 72 carriers 35 are used, 16 carriers include first strands 12, while the remaining carriers 35 (i.e., 56 carriers) include second strands 14. Thus, the number of second strands 14 is typically larger than the number of first strands 12. In some embodiments, a ratio of the number of second strands 14 to first strands 12 is at least about 1.5:1, at least about 2:1, at least about 3:1, at least about 4:1, or at least about 5:1. Thus, in some embodiments, a greater number of second strands 14 are employed which ensures that tubular member 11 is not too stiff, and the incorporation of larger diameter first strands 12 are used in only those areas where increased stiffness is needed.

Example braiding machines 30 may be adapted to perform the processes described herein. These braiding machines 30 may be modified to provide a number of variable braid patterns and to handle different strand materials and numbers of strands. Braiding machines 30 used in accordance with the embodiments described herein may include multiple carriers 35 of strands 12, 14. Braiding machines 30 may be configured to braid, for example, strands 12, 14 using 8-288 filament carriers.

Individual carriers 35 shown in FIG. 13 are divided into two sets of strands (12 or 14), and each strand (12 or 14) extends from a respective spool to mandrel 32. In some cases, however, more than two sets of strands (12 or 14) may be used, such as 3 or 4 sets of strands (12 or 14), depending on the desired braid pattern. In FIG. 13, the spools of each set are arranged circumferentially about a longitudinal axis X of mandrel 32 (i.e., the axis of braid formation, shown in FIG. 12), with the spools carrying the first set of strands (12 or 14) rotating in a generally circular manner in a first direction about the axis X and the spools carrying the second set of strands (12 or 14) rotating in a generally circular manner in a second direction about the axis. Thus, the first and second sets rotate in opposite directions within a plane YZ (shown in FIG. 12) that is generally perpendicular to the longitudinal axis X. For example, the spools of one set of strands (12 or 14) (e.g., the even-numbered spool carriers 35 shown in FIG. 13) may move in the clockwise direction CW, and the spools of the second set of strands (12 or 14) (e.g., the strands corresponding to the odd-numbered spool carriers shown in FIG. 13) may move in a counter-clockwise direction CCW, as illustrated. This action forms tubular member 11 about mandrel 32 with strands 12, 14 that are woven over and under each other in a braided configuration, as shown in FIG. 12. In one embodiment, strands 12, 14 are pulled in a direction that is at an angle to and away from the plane YZ of spool carriers 35 (shown in FIG. 12). The resulting tubular member 11 thus comprises braided strands 12, 14 that traverse the circumference of the mandrel 32.

Groups of carriers 35 may be employed for strands 12, 14. As discussed above with reference to FIG. 8, four groups of first strands 12 may be used to create stiff regions radially opposite one another (e.g., stiff regions 21a, 21b shown in FIGS. 1-3 and 7). Thus, with reference to FIG. 13, a plurality of groups of carriers 35 may include spools of strands 12 or 14 to create cross-over locations or intersections to define regions of variable radial stiffness. For example, spool carriers 1-4, 8-12, and 16-20, and 24-28 may include spools of first strands 12, while the remaining spool carriers may include spools of second strands 14. Thus, four groups of spool carriers 35 may be used to carry first strands 12 to define stiff regions that are radially opposite one another as strands are wound about mandrel 32. However, in some instances, different groups of first strands 12 may be chosen that create stiff regions that are not radially opposite one another, such as where an odd number of groups of first strands 12 are employed. In one embodiment, spools of second strands 14 include a larger number of wires than spools of first strands 12. In some embodiments, the pic count (i.e., the number of strand crossovers per inch, or other lineal measure) may range from 20 to 78 PPI (pics per inch), although a higher or lower pic count may be used depending on the desired characteristics to be imparted to tubular member 11. For example, a higher pic count could be used to provide increased stiffness. According to one embodiment, strands 12, 14 may be braided onto mandrel 32 having a diameter ranging from approximately 3 mm to approximately 40 mm.

Depending on the configuration of braiding machine 30, many different braid patterns may be formed. For example, in one braid pattern, a single strand 12 or 14, if followed, may pass over one strand (12 or 14) of the opposite helix wind (the opposite "hand"), under the next strand of opposite helical wind, over the next strand of the opposite helix wind, etc., in a repeating pattern. As another example, one or more strands (12 or 14) of one hand can also pass over one or more strands of the opposite hand and then under one or more strands of the opposite hand in a repeating pattern.

Once strands 12, 14 have been braided onto mandrel 32 to form braided fabric 19 as described above, tubular member 11 may undergo further processing to prepare tubular member 11 or a portion of tubular member 11 for use in a particular device or application. For example, medical device 10 shown in FIGS. 1-3 may be made by cutting an appropriately sized tubular member 11 from braided fabric 19 formed on mandrel 32. When cutting braided fabric 19 to the desired dimensions, one may solder, braze, weld, coat, glue, clamp, tie, or otherwise affix the ends of the cut portion together to minimize the risk of unraveling the braid pattern.

Tubular member 11 may be cut to align strands 12, 14 at desired locations between proximal 13 and distal 15 ends. For example, locations of intersections of first strands 12 may be chosen to align with disks 20, 22. Thus, one or more regions may be selected where first strands 12 intersect one another to align with locations where greater stiffness is desired (e.g. along perimeter 25 of disks 20, 22 and/or 90 degree offset on waist 26 shown in FIG. 4) Likewise, locations where strands 12 do not intersect one another may be chosen to align with regions where less stiffness is needed, such as in areas where limited or no contact with the target site is desired. If necessary and in order to aid in identifying locations where first strands 12 intersect, tubular member 11 may be pulled down or axially elongated so that first strands 12 intersect at co-linear locations (see e.g., FIGS. 10 and 11).

Once an appropriately sized piece of braided fabric 19 is obtained as tubular member 11 and the appropriate locations of the intersections of first strands 12 have been determined, tubular member 11 may be deformed to generally conform to a surface of a molding element. For example, locations where first strands 12 intersect one another may be placed on a mold or mandrel that align with locations on the mold for forming one or more disks. Deforming tubular member 11 may reorient the relative positions of the braided strands 12, 14 from their original order to a second, reoriented configuration. To minimize any undesirable changes to the braid pattern during significant shape forming, the braid may be stabilized by heat setting the braid pattern on mandrel 32 or removing tubular member 11 from mandrel 32 and heat setting the braid pattern prior to shape forming into the mold. This may help to substantially lock in the braid pattern while allowing the relative strand 12, 14 reorientation to achieve the shape formation of the mold. In other cases, however, heat setting may not be necessary. In addition, it is understood that braided fabric 19 may be cut to desired length of tubular member 11 before or after heat setting tubular member 11 into a desired shape.

The shape of the molding element should be selected to deform tubular member 11 into substantially the desired shape (e.g., the shape of tubular member 11 shown in FIGS. 1 and 2). In medical device applications, for example, the shape of the molding element may be selected to deform tubular member 11 into substantially the shape of the desired medical device when unconstrained (e.g., deployed from a delivery device). Once the molding element is assembled with t tubular member 11 generally conforming to a molding surface of that element, tubular member 11 can be subjected to a heat treatment while it is maintained in contact with that molding surface. For example, suitable heat treatments of Nitinol wire to set a desired shape are well known in the art. It has been found that holding a Nitinol fabric at about 500° C. to about 550° C. for a period of about 1 to about 30 minutes, depending on the softness or hardness of medical device 10 to be made, will tend to set the braided fabric 19 in its deformed state, such that the braided fabric 19 conforms to the molding surface of the molding element. At lower temperatures the heat treatment time will tend to be greater (e.g., about one hour at about 350° C.), and at higher temperatures the time will tend to be shorter (e.g., about 30 seconds at about 900° C.).

Accordingly, in some embodiments, at least some of strands 12, 14 comprise a shape memory alloy such that the resulting tubular member 11 is configured to have an expanded configuration when tubular member 11 is not constrained (radially and/or axially) and to have a reduced configuration when tubular member 11 is constrained. In one example, medical device 10 may be axially elongated from an expanded configuration to a reduced diameter. In this way, tubular member 11 may be configured to self-expand from the reduced configuration to the expanded configuration when an applied constraint (such as a delivery device inside of which medical device 10 is disposed in the reduced configuration) is removed.

Figure 14:
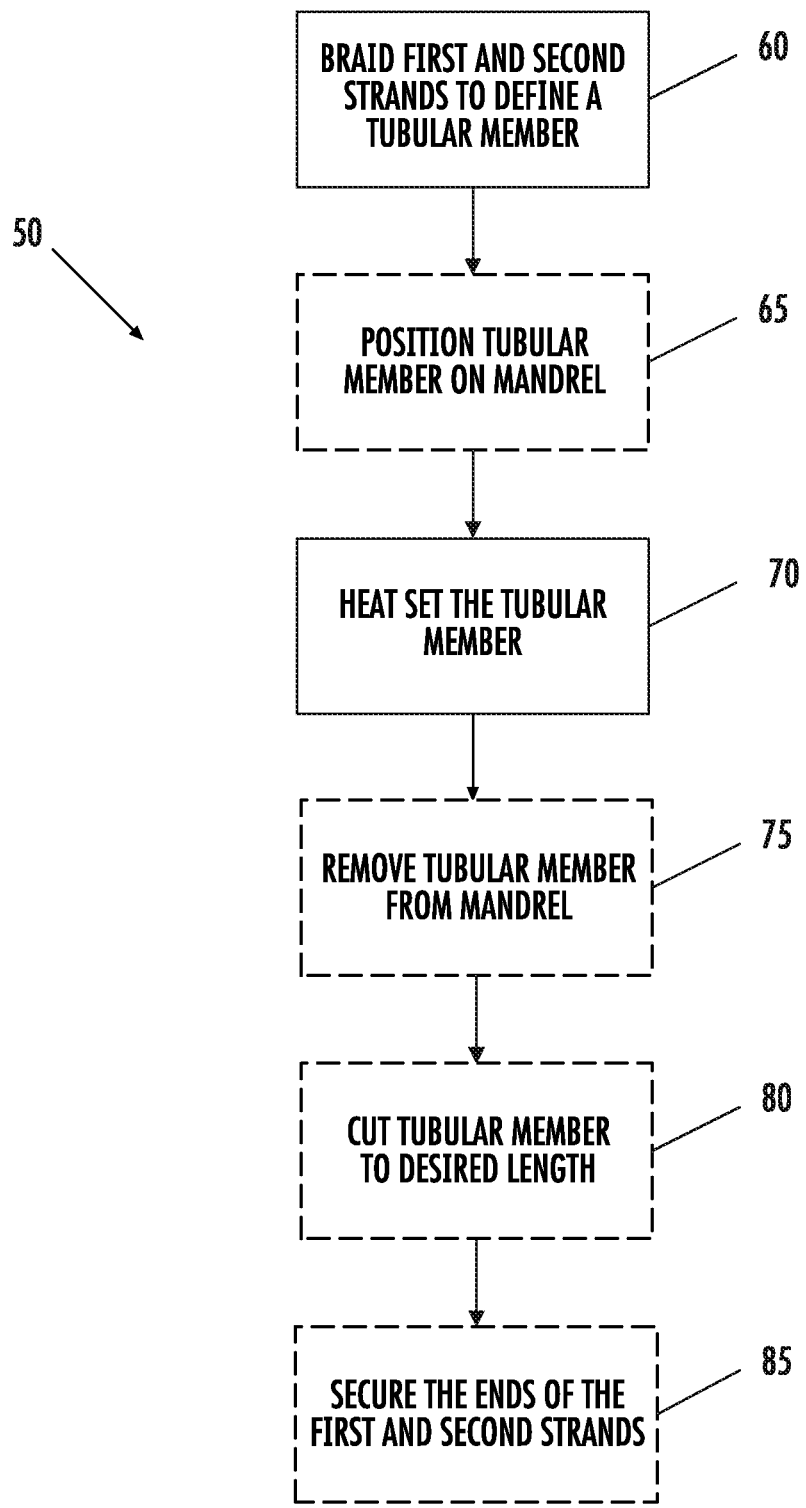
FIG. 14 is a flowchart illustrating a method of manufacturing a medical device according to one embodiment of the present disclosure.

FIG. 14 illustrates one embodiment of method 50 for manufacturing a medical device, such as medical device 10 described above with reference to FIGS. 1-3. Method 50 generally includes braiding a plurality of first strands (e.g., first strands 12 discussed above) and a plurality of second strands (e.g., second strands 14 discussed above) to define a tubular member (e.g., tubular member 11 discussed above) having at least one layer of braided fabric (e.g., braided fabric 19 described above) (Block 60). Groups of strands may be braided on a mandrel as discussed above (e.g., mandrel 32 discussed above). The first strands have a diameter larger than the second. The first strands are braided such that the first strands intersect one another at one or more locations between the proximal and distal ends of the tubular member to define at least one region of increased radial stiffness (see e.g., stiff regions 21a, 21b, 21c shown in FIGS. 1-3) in relation to one or more locations where the plurality of second strands intersect one another or the first strands are not located. After braiding strands to form a tubular member formed of a braided fabric, the tubular member may be positioned on a mandrel having a desired shape (Block 65). For instance, the tubular member could be positioned on a mandrel having a shape including one or more disks (e.g., disks 20, 22 discussed above), wherein the stiff regions are chosen to align with the disks. However, the tubular member may remain on the mandrel on which it was initially braided (Block 60) if the mandrel includes the final desired shape of the medical device. Method 50 further includes heat setting the tubular member to define an expanded preset configuration (Block 70). Additional steps of method 50 may include removing the heat set tubular member from the mandrel (Block 75) and cutting the tubular member to a desired length (Block 80). However, it is understood that the tubular member may be cut to a desired length prior to heat setting the braided fabric in some embodiments, and the braided fabric may not need to be cut if braided to the desired length. In one example, method 50 may further include securing free ends of the first strands and the second strands at each of the proximal and distal ends of the tubular member to prevent the strands from unraveling (Block 85).

One embodiment of method 100 for delivering a medical device to a target site, such as medical device 10 described above is summarized in FIG. 15. Any suitable delivery device may be used to deliver the medical device. For example, the delivery device may include a delivery wire configured to releasably attach to and detach from the medical device.

The medical device may be attached to the delivery device, such as via attachment of a delivery wire to the medical device (Block 110). For example, the delivery device may attach to a proximal clamp in a threaded engagement (e.g., proximal clamp 16 shown in FIGS. 1A and 4). Attachment of the medical device may occur, in some cases, at a facility at which the delivery device is manufactured, such that an operator of the delivery device receives the delivery device and the medical device already attached. Alternatively, the medical device may be attached to the delivery device at the time of use or implantation or at a separate location from where the delivery device is manufactured. The delivery device and the medical device may then be advanced through a delivery catheter to a target site while the medical device is in a reduced configuration (Block 120). As discussed above, the medical device is configured to have an expanded configuration when not constrained (radially and/or axially) and to have a reduced configuration when constrained. For example, the medical device may be axially elongated from an expanded configuration to a reduced diameter and positioned within the delivery catheter. The medical device may then be deployed at the target site (Block 140) to assume the expanded configuration (e.g., medical device 10 shown in FIG. 1). Thus, the medical device may be configured to self-expand from the reduced configuration to the expanded configuration when an applied constraint (e.g. a delivery catheter inside of which the medical device is disposed in the reduced configuration) is removed. In one embodiment, deployment of the medical device may occur through self expansion of the medical device (e.g., after withdrawing the delivery catheter at Block 140), while in other embodiments, the delivery device may also or alternatively be displaced such that the medical device at least partially returns to the expanded configuration. In some instances, the medical device may be positioned at the target site such that the stiff region(s) of the medical device aligns with a desired location to provide a clamping force to retain the medical device at the target site. For example, the distance between the disks may be less than a thickness of the target site such that the disks are clamped to the target site. Likewise soft region(s) of the medical device may be aligned with a desired location at the target site where minimal or no contact with the target site is necessary.

The medical device may then be detached from the delivery device (Block 160), such as be threadably detaching the delivery device from the proximal clamp. The delivery device and the delivery catheter may be withdrawn from the target site (Block 170). In some cases, at Block 150, the medical device may be recaptured such as in cases where the medical device is to be repositioned (e.g., when the medical device is deployed in an incorrect location or could be more favorably positioned). For example, where the delivery catheter is withdrawn proximally to partially deploy the medical device, the delivery catheter may be displaced distally to radially constrain the medical device and force the medical device within the delivery catheter. In instances where the medical device comprises a tubular member formed from braided fabric that is deployed within the body, over time thrombi will tend to collect on the surface of the braided strands when the medical device is deployed in a patient to occlude the target site.

Figure 15:
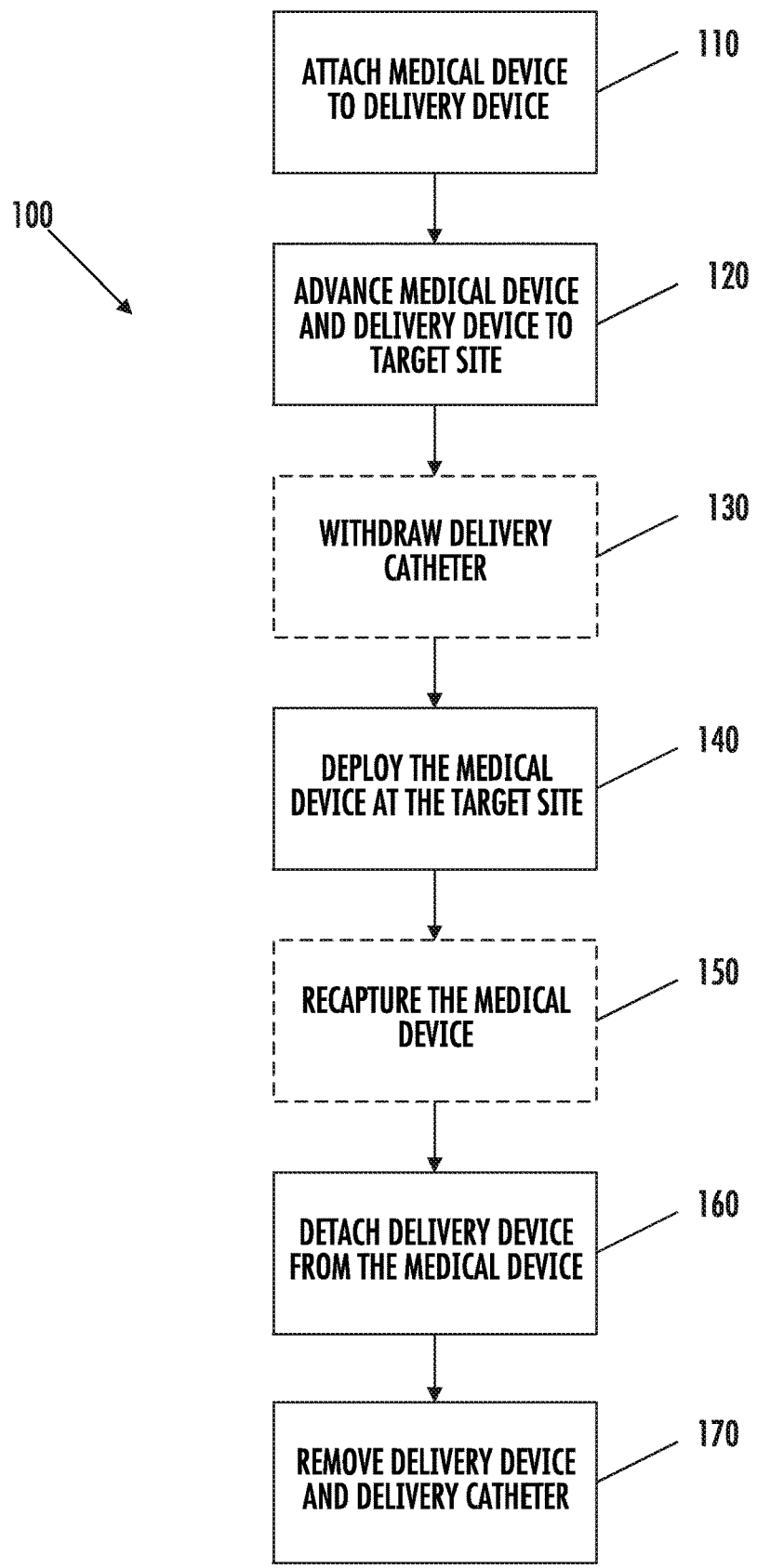
FIG. 15 is a flowchart illustrating a method of delivering a medical device to a target site according to an embodiment of the present disclosure.

The method depicted in FIGS. 14 and 15 and described above represents only one possible method for manufacturing and delivering a medical device for treating a target site. It is understood that the illustrated steps in FIGS. 14 and 15 may be performed in any desired order and should not be limited to the illustrated embodiments. In some embodiments, certain ones of the steps described above may be modified, omitted, or further amplified. Furthermore, in some embodiments, additional optional steps may be included, some examples of which are shown in dashed lines in FIGS. 14 and 15. Modifications, additions, omission, or amplifications to the steps above may be performed in any order and in any combination. The particular methods of manufacturing and delivery will depend on the desired configuration of the medical device, the patient's anatomy, the condition and location of the target site, the preferences of the practitioner, and/or other considerations.

A medical device configured according to the embodiments described above may provide for several advantages. For example, the medical device includes asymmetric radial stiffness whereby the medical device exhibits stiff and soft regions (see e.g., FIGS. 3 and 7). In some instances, the medical device may exhibit asymmetric radial stiffness but symmetric axial stiffness (see e.g., FIGS. 9-11). Such variable stiffness allows the mechanical properties of the medical device to be varied for a particular target site. For example, softer regions may be positioned so as to not be in contact with the target site, while stiffer regions may be positioned to contact the target site and anchor the medical device at the target site. Conventional devices rely on the formed geometry or the heat treatment of the device to create variable stiffness. In contrast, medical devices according to embodiments of the present disclosure provide variable stiffness independent of the device geometry and greater variability in stiffness than conventional methods. Thus, the medical devices may be more easily customized to include specific mechanical properties (e.g., asymmetric radial stiffness and/or symmetric axial stiffness) for more effectively treating a target site based on the desired function of the medical devices. In addition, the stiff and soft regions are able to be aligned with various features of the medical device, such as along an outer perimeter of disks or along a waist of the medical device. By selectively locating stiff regions on the medical device, sufficient anchoring and stiffness may be provided at the target site. Likewise, providing soft regions at particular locations may allow smaller diameter and softer strands in at least some regions, which may offset any additional profile size resulting from the larger diameter and stiffer stands in the stiff regions. Moreover, embodiments of the present disclosure reduce the impact of fatigue performance that would otherwise occur if variable heat treatment was employed.

Many modifications and other embodiments of the disclosure set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device for treating a target site, the medical device comprising:
   a tubular member having a proximal end and a distal end and formed from at least one layer of braided fabric, the tubular member having an expanded configuration comprising a pair of disks and a reduced diameter waist extending therebetween when deployed at the target site and a reduced configuration for delivery to the target site, a pair of terminal members wherein a proximal terminal member is secured to a proximal end of the tubular member and a distal terminal member is secured to a distal end of the tubular member, wherein the reduced diameter waist is recessed such that the proximal terminal member is at least partially surrounded by the reduced diameter waist in the expanded configuration, wherein each disk of the pair of disks comprises an outer layer of fabric and an inner layer of fabric, wherein the pair of disks comprises a proximal disk having a diameter smaller than a diameter of a distal disk, wherein the proximal terminal member is distal of the proximal disk, wherein the distal terminal member is distal of the distal disk, and wherein a portion of a distal surface of the proximal disk extending from an outer edge thereof to a point a distance from the outer edge is substantially perpendicular to a longitudinal axis extending from a proximal end to a distal end of the medical device,
   wherein the at least one layer of braided fabric comprises a plurality of first strands having a first diameter and a plurality of second strands having a second diameter, the first diameter being larger than the second diameter,
   wherein the plurality of first strands and the plurality of second strands are intertwined with one another to define the at least one layer of braided fabric, and
   wherein the plurality of first strands intersect one another at one or more locations between the proximal and distal ends of the tubular member to define at least one region of increased stiffness in relation to one or more locations where the plurality of first strands do not intersect one another.

2. The medical device of claim 1, wherein the plurality of first strands and the plurality of second strands comprise a shape memory metal material.

3. The medical device of claim 1, wherein the plurality of first strands intersect one another at least partially along an outer perimeter of at least one of the pair of disks.

4. The medical device of claim 1, wherein the plurality of first strands intersect one another at least partially along an outer perimeter of each of the pair of disks and at least partially along an outer perimeter of the reduced diameter waist.

5. The medical device of claim 1, wherein the plurality of first strands intersect at a plurality of locations between the proximal and distal ends of the tubular member to define a plurality of corresponding regions of increased radial stiffness.

6. The medical device of claim 1, wherein each of the terminal members secures free ends of each of the plurality of first strands and the plurality of second strands.

7. The medical device of claim 1, wherein a ratio of the first diameter to the second diameter is at least about 2:1.

8. The medical device of claim 1, wherein a ratio of the number of the plurality of second strands to the plurality of first strands is at least 2:1.

9. The medical device of claim 1, wherein the plurality of first strands intersect one another at radially opposite locations between the proximal and distal ends of the tubular member.

10. A medical device for treating a target site, the medical device comprising:
    a plurality of first strands having a first diameter;
    a plurality of second strands having a second diameter smaller than the first diameter, the plurality of second strands intertwined with the plurality of first strands to define at least one layer of braided fabric having regions of varying radial stiffness; and
    a tubular member formed from the at least one layer of braided fabric, the tubular member having an expanded configuration comprising a pair of disks and a reduced diameter waist extending therebetween for deployment at the target site and a reduced configuration for delivery to the target site, a pair of terminal members wherein a proximal terminal member is secured to a proximal end of the tubular member and a distal terminal member is secured to a distal end of the tubular member, wherein the reduced diameter waist is recessed such that the proximal terminal member is at least partially surrounded by the reduced diameter waist in the expanded configuration, wherein each disk of the pair of disks comprises an outer layer of fabric and an inner layer of fabric, wherein the pair of disks comprises a proximal disk having a diameter smaller than a diameter of a distal disk, wherein the proximal terminal member is distal of the proximal disk, wherein the distal terminal member is distal of the distal disk, and wherein a portion of a distal surface of the proximal disk extending from an outer edge thereof to a point a distance from the outer edge is substantially perpendicular to a longitudinal axis extending from a proximal end to a distal end of the medical device.

11. The medical device of claim 10, wherein the plurality of first strands intersect one another at one or more locations on the tubular member to define at least one region of increased radial stiffness in relation to one or more locations where the plurality of first strands do not intersect one another.

12. The medical device of claim 11, wherein the plurality of first strands intersect at a plurality of locations between to define a plurality of corresponding regions of increased radial stiffness.

13. The medical device of claim 10, wherein the plurality of first strands intersect one another at least partially along a circumference of the tubular member.

14. The medical device of claim 10, wherein the plurality of first strands intersect one another at radially opposite locations on the tubular member.

15. The medical device of claim 10, wherein the plurality of first strands intersect one another at a plurality of co-linear locations on the tubular member.

16. A medical device for treating a target site, the medical device comprising:
- a plurality of first strands having a first diameter;
- a plurality of second strands having a second diameter smaller than the first diameter, the plurality of second strands intertwined with the plurality of first strands to define at least one layer of braided fabric having a braid pattern; and
- a tubular member formed from the at least one layer of braided fabric, the tubular member having an expanded configuration for deployment at the target site and a reduced configuration for delivery to the target site, the tubular member comprising a pair of disks and a reduced diameter waist extending therebetween in the expanded configuration, a pair of terminal members wherein a proximal terminal member is secured to a proximal end of the tubular member and a distal terminal member is secured to a distal end of the tubular member, wherein the reduced diameter waist is recessed such that the proximal terminal member is at least partially surrounded by the reduced diameter waist in the expanded configuration, wherein each disk of the pair of disks comprises an outer layer of fabric and an inner layer of fabric, wherein the pair of disks comprises a proximal disk having a diameter smaller than a diameter of a distal disk, wherein the proximal terminal member is distal of the proximal disk, wherein the distal terminal member is distal of the distal disk, wherein a portion of a distal surface of the proximal disk extending from an outer edge thereof to a point a distance from the outer edge is substantially perpendicular to a longitudinal axis extending from a proximal end to a distal end of the medical device, and wherein at least one disk of the pair of disks comprises at least one stiff region and at least one soft region resulting from the braid pattern of the first and second strands.

17. A method of manufacturing a medical device, the method comprising:
- braiding a plurality of first strands and a plurality of second strands to define a tubular member having at least one layer of braided fabric, the plurality of first strands having a first diameter and the plurality of second strands having a second diameter, the first diameter being larger than the second diameter; and
- heat setting the tubular member to define an expanded preset configuration, the tubular member having a proximal end and a distal end and comprising a pair of disks and a reduced diameter waist extending therebetween, a pair of terminal members wherein a proximal terminal member is secured to a proximal end of the tubular member and a distal terminal member is secured to a distal end of the tubular member, wherein the reduced diameter waist is recessed such that the proximal terminal member is at least partially surrounded by the reduced diameter waist in the expanded configuration, wherein each disk of the pair of disks comprises an outer layer of fabric and an inner layer of fabric, wherein the pair of disks comprises a proximal disk having a diameter smaller than a diameter of a distal disk, wherein the proximal terminal member is distal of the proximal disk, wherein the distal terminal member is distal of the distal disk, and wherein a portion of a distal surface of the proximal disk extending from an outer edge thereof to a point a distance from the outer edge is substantially perpendicular to a longitudinal axis extending from a proximal end to a distal end of the medical device,
- wherein braiding comprises braiding the plurality of first strands such that the plurality of first strands intersect one another at one or more locations between the proximal and distal ends of the tubular member to define regions of varying radial stiffness between the proximal and distal ends of the tubular member.

18. The method of claim 17, wherein braiding comprises braiding the plurality of first strands such that the plurality of first strands intersect one another to define at least one region of increased radial stiffness in relation to one or more locations where the plurality of first strands do not intersect one another.

19. The method of claim 18, wherein braiding comprises braiding the plurality of first strands such that the plurality of first strands intersect one another at a plurality of locations between the proximal and distal ends of the tubular member to define a plurality of corresponding regions of increased radial stiffness.

20. The method of claim 17, wherein braiding comprises braiding the plurality of first strands such that the plurality of first strands intersect one another at least partially along a circumference of the tubular member.

21. The method of claim 17, wherein braiding comprises braiding the plurality of first strands such that the plurality of first strands intersect one another at radially opposite locations between the proximal and distal ends of the tubular member.

22. The method of claim 17, wherein braiding comprises braiding the plurality of first strands such that the plurality of first strands intersect one another at a plurality of co-linear locations between the proximal and distal ends of the tubular member.

23. The method of claim 17, further comprising securing free ends of each of the plurality of first strands and the plurality of second strands at each of the proximal and distal ends of the tubular member.

24. The method of claim 17, wherein braiding comprises braiding the plurality of first strands such that the plurality of first strands intersect one another at least partially along an outer perimeter of at least one of the pair of disks.

25. The method of claim 17, further comprising loading the plurality of first strands and the plurality of second strands on respective carriers prior to braiding the plurality of first strands and the plurality of second strands.

* * * * *